(12) United States Patent
Zhang et al.

(10) Patent No.: US 11,959,128 B2
(45) Date of Patent: Apr. 16, 2024

(54) METHOD FOR DETERMINING CONTENT OF CELL-FREE FETAL DNA AND DEVICE FOR IMPLEMENTING METHOD

(71) Applicant: BERRY GENOMICS CO., LTD, Beijing (CN)

(72) Inventors: Xiaojie Zhang, Beijing (CN); Tao Cheng, Beijing (CN); Xiangbin Chen, Beijing (CN); Jianguang Zhang, Beijing (CN)

(73) Assignee: BERRY GENOMICS CO., LTD., Beijing (CN)

( * ) Notice: Subject to any disclaimer, the term of this patent is extended or adjusted under 35 U.S.C. 154(b) by 1253 days.

(21) Appl. No.: 16/469,102

(22) PCT Filed: Mar. 15, 2017

(86) PCT No.: PCT/CN2017/076826
§ 371 (c)(1),
(2) Date: Jun. 12, 2019

(87) PCT Pub. No.: WO2018/107598
PCT Pub. Date: Jun. 21, 2018

(65) Prior Publication Data
US 2020/0080138 A1    Mar. 12, 2020

(30) Foreign Application Priority Data
Dec. 14, 2016   (CN) .......................... 201611153694.8

(51) Int. Cl.
| | | |
|---|---|---|
| *C12Q 1/6827* | (2018.01) | |
| *C12Q 1/6869* | (2018.01) | |
| *C12Q 1/6883* | (2018.01) | |
| *C40B 40/08* | (2006.01) | |
| *G16B 20/10* | (2019.01) | |
| *G16B 30/10* | (2019.01) | |

(52) U.S. Cl.
CPC .......... *C12Q 1/6827* (2013.01); *C12Q 1/6869* (2013.01); *C12Q 1/6883* (2013.01); *C40B 40/08* (2013.01); *G16B 20/10* (2019.02); *G16B 30/10* (2019.02); *C12Q 2535/122* (2013.01); *C12Q 2563/159* (2013.01)

(58) Field of Classification Search
None
See application file for complete search history.

(56) References Cited

U.S. PATENT DOCUMENTS

2013/0237431 A1   9/2013   Lo et al.
2016/0203260 A1   7/2016   Lo et al.

FOREIGN PATENT DOCUMENTS

| CN | 102108406 A | 6/2011 |
| CN | 102791881 A | 11/2012 |
| CN | 104951671 A | 9/2015 |
| CN | 106156543 A | 11/2016 |
| WO | WO 2016/112851 A1 | 7/2016 |

OTHER PUBLICATIONS

Yu et al. "Size-based molecular diagnostics using plasma DNA for noninvasive prenatal testing." PNAS. vol. 111:23, pp. 8583-8588. (Year: 2014).*
Yuan et al. "Feasibility Study of Semiconductor Sequencing for Noninvasive Prenatal Detection of Fetal Aneuploidy." Clinical Chemistry. vol. 59:5, pp. 846-849. (Year: 2013).*
Macaulay and Voet. "Single Cell Genomics: Advances and Future Perspectives." PLoS. vol. 10(1): e1004126, pp. 1-9. (Year: 2014).*
Li et al. "A survey of sequence alignment algorithms for next-generation sequencing." Briefings in Bioinformatics. vol. 2:5, pp. 473-483. (Year: 2010).*
Voelkerding et al. "Next-Generation Sequencing: From Basic Research to Diagnostics." Clinical Chemistry. vol. 55:4, pp. 641-658. (Year: 2009).*
Chandrananda et al. "Investigating and Correcting Plasma DNA Sequencing Coverage Bias to Enhance Aneuploidy Discovery." PloS ONE, vol. 9(1): e86993. doi:10.1371/journal.pone.0086993, pp. 1-14. (Year: 2014).*
Li et al. "Mapping short DNA sequencing reads and calling variants using mapping quality scores." Genome Research, vol. 18, pp. 1851-1858. (Year: 2008).*
Karlsson et al. "Amplification-free sequencing of cell-free DNA for prenatal non-invasive diagnosis of chromosomal aberrations." Genomics, 2015, vol. 105, pp. 150-158. (Year: 2015).*
Fan et al., "Analysis of the Size Distributions of Fetal and Maternal Cell-Free DNA by Paired-End Sequencing," *Clinical Chemistry*, 56(8):1279-1286 (2010).
International Search Report dated Sep. 4, 2017, in International Application No. PCT/CN2017/076826.
Wang et al., "Application of non-invasive prenatal DNA test in screening of Down's syndrome," *Medical Journal of Chinese People's Health*, 26(10):1-3 (2014).
Yu et al., "Size-based molecular diagnostics using plasma DNA for noninvasive prenatal testing," *PNAS*, 111(23):8583-8588 (2014).
Extended European Search Report dated Jun. 8, 2020, in European Patent Application No. 17879950.8.
Office Action dated Sep. 29, 2019, in Chinese Patent Application No. 201611153694.8, with English translation of Search Report.
Yan, Ling, et al. "Non-invasive determination of fetal gender using microarray coupled with microemulsions PCR in first trimester." *Modern Medical Journal* 2 (2007).

* cited by examiner

Primary Examiner — John S Brusca
Assistant Examiner — Steven W. Bailey
(74) *Attorney, Agent, or Firm* — Arnold & Porter Kaye Scholer LLP

(57) ABSTRACT

The present invention relates to the field of noninvasive prenatal gene testing by high-through sequencing technologies. Particularly, the present application relates to a method for determining the content of cell-free fetal DNA in maternal peripheral blood.

6 Claims, 2 Drawing Sheets

METHOD FOR DETERMINING CONTENT OF CELL-FREE FETAL DNA AND DEVICE FOR IMPLEMENTING METHOD

TECHNICAL FIELD

The present invention relates to the field of noninvasive prenatal gene testing using high-through sequencing technologies. Particularly, the present application relates to a method for determining the content of cell-free fetal DNA in maternal peripheral blood.

BACKGROUND

The current noninvasive prenatal gene testing is carried out by collecting maternal peripheral blood, extracting cell-free plasma DNA contained therein, performing the next generation high-through sequencing and bioinformatics analysis, and finally evaluating the risk of developing chromosomal aneuploidy (such as trisomy 21 (T21) which is also called Down's syndrome, trisomy 18, and trisomy 13) in a fetus. The best timing for such test is over 12 week's gestation. Said testing has the advantages of noninvasive sample collection, no risk of abortion, high sensitivity and high accuracy, thus has been widely used in the prenatal clinical detection.

The presence of cell-free fetal DNA was first confirmed in 1997. Lo et al. detected cell-free fetal DNA (cffDNA) in maternal plasma of women bearing male fetuses by PCR amplifying the Y-chromosome specific DNA fragments from the maternal peripheral plasma (see Lo, Y. M. et al., Presence of fetal DNA in maternal plasma and serum, Lancet, 1997. 350(9076): p. 485-7). Afterwards, a number of reports have disclosed the presence of both intact fetal cell and free-circulating cell-free nucleic acids in the maternal blood circulation system, making it possible to use cffDNA in noninvasive prenatal evaluation of the genetic characteristics of a fetus.

Further studies have shown that the cell-free DNA present in the maternal peripheral plasma as small fragments with an average length of 166 bp. The content of cell-free DNA in the plasma is very low, generally is only nanograms per milliliter of blood plasma. However, the content of cell-free DNA originating from a fetus is even lower, which only accounts for 3%-6% of the total cell-free DNA (this ratio increases slowly along with the gestation weeks). In addition, the half-life of the cell-free fetal DNA is very short, which is around 16 minutes, thus it cannot be detected in the maternal peripheral blood obtained 2 hours after normal delivery. This property of rapid degradation of the cell-free fetal DNA makes it an optimal material for noninvasive prenatal testing.

In 2008, Chiu et al systematically proved for the first time that cffDNA in the maternal peripheral plasma can be used to achieve noninvasive prenatal detection of aneuploidy (see Chiu, R. W. et al., Noninvasive prenatal diagnosis of fetal chromosomal aneuploidy by massively parallel genomic sequencing of DNA in maternal plasma. Proc Natl Acad Sci USA, 2008. 105(51): p. 20458-63). The employed principle is as follows: taking the most common Down's syndrome (T21) in birth-defects as an example, normal fetus and normal woman both have 2 chromosome 21, while fetus with Down's syndrome has 3 chromosome 21. Assuming in the maternal peripheral blood, the cell-free fetal DNA is 20% and the cell-free maternal DNA per se is 80%, for simplicity, assuming it is 10 copies of DNA in total, thus, in the peripheral blood plasma of a woman bearing a normal fetus, the cell-free DNA of chromosome 21 is 10 copies, wherein 2 copies originate from the fetus, and 8 copies originate from the woman. On the other side, for a woman bearing a T21 fetus, it can be calculated that there are 11 copies of cell-free DNA for chromosome 21, wherein 3 copies originate from the fetus, and 8 copies originate from the woman. Thus, the ratio of cell-free DNA of chromosome 21 between the woman bearing a T21 fetus and the woman bearing a normal fetus is 11:10. Similarly, in the cases wherein the content of cell-free fetal DNA is 5%, the ratio of cell-free DNA of chromosome 21 between the woman bearing a T21 fetus and the woman bearing a normal fetus is 10.25:10. Accordingly, without isolating cell-free DNA originated from the fetus, it can be determined that generally there is a small increment in the total content of cell-free DNA of chromosome 21 in the peripheral plasma from a woman bearing a T21 fetus. Theoretically, by distinguishing such small increment, cffDNA can be used for prenatal detection of chromosomal abnormality in a fetus.

Thus, the content of cell-free fetal DNA directly affects the ratio of chromosomes to be detected, thereby affecting the accuracy of the noninvasive prenatal testing eventually. In other words, the content of cell-free fetal DNA is an important factor contributing to the accuracy of detection. When the content of cell-free fetal DNA is low, the detection results may be false negative or false positive. In 2014, Hudecova et al reported that for a woman bearing a male fetus, the content of cell-free fetal DNA cff % can be easily calculated based on the percentage (chrY %) of chromosome Y sequence reads relative to the reads aligned to autosomes (as the chromosome Y is only contained in the male fetus but not in the maternal genome) (see Hudecova, I., et al., Maternal plasma fetal DNA contents in pregnancies with low and high risks for fetal chromosomal aneuploidies. PLoS One, 2014. 9(2): p. e88484). However, this method is not applicable to a female fetus.

In 2014, Yu et al found that the size of cell-free DNA fragment derived from the fetus is generally shorter than that derived from the mother, and further verified that the size ratio of shorter fragments (100-150 bp) and longer fragments (163-169 p) is linearly correlated with the content of cell-free fetal DNA by performing high-throughput paired-end sequencing and calculating the distribution of the cell-free DNA fragments in plasma (see Yu, S. C. et al., Size-based molecular diagnostics using plasma DNA for noninvasive prenatal testing, Proc Natl Acad Sci USA, 2014, 111(23):8538-8588). This opens a door for the detection of the content of cell-free fetal DNA, i.e., it can be calculated by the size distribution of the cell-free DNA fragments in plasma. Said method has also been proved to be applicable in clinic and is independent of the sex of the fetus.

However, existing noninvasive prenatal testing commonly uses single-end sequencing. As indicated above, the method of Yu et al is based on the results of paired-end sequencing. It is well known that the cost and duration of paired-end sequencing are higher than those of single-end sequencing, and the hardware support from the service required for analysis is also increased. Thus, there is a need for a method of determining the content of cell-free fetal DNA based on the results of single-end sequencing, thereby reducing the cost and timing required for the noninvasive prenatal testing.

DESCRIPTION

The content of cell-free fetal DNA is a key determinant to evaluate the reliability of a noninvasive prenatal testing.

Based on the single-end sequencing commonly used in the noninvasive prenatal testing fields, the inventors propose an effective method of determining the content of cell-free fetal DNA by high-throughput single-end sequencing.

The invention is based on the following fact: the high-throughput single-end sequencing has certain probability to simultaneously detect both ends of a double strand DNA fragment derived from the same DNA molecule. Specifically, according to a standard sequencing procedure, the probability of detecting both ends of the same fragment by a single-end sequencing can be calculated as follows:

(1) Taking Illumina NextSeq platform as an example, at least 1.3 mL DNA solution at a concentration of 2.5 pmol/L will be required to sequence one Illumina NextSeq High-throughput Flowcell, wherein there are around $2.0 \times 10^9$ ($1.3 \times 10^{-3} \times 2.5 \times 10^{-12} \times 6 \times 10^{23}$) DNA molecules in total.

(2) Generally, the results include at least 400M sequences. Thus, the probability of each DNA strand to be detected is around 0.2 ($400 \times 10^6 / 2.0 \times 10^9$). Accordingly, the probability of simultaneously detecting a double strand molecule is around 0.04 ($0.2 \times 0.2$).

(3) Each sample has a throughput of about 4M sequences. Thus, the number of detected double strand molecules can reach up to $1.6 \times 10^5$ ($4 \times 10^6 \times 0.04$), that is, 160,000 paired-end events.

Based on the above theory, a significant number of paired-end sequencing data can be obtained from the single-end sequencing results (Example 1 and FIG. 1), thereby the size distribution of plasma DNA fragment can be calculated according to the localization of the paired-end sequence in the genome, which enables efficient calculation of the content of cell-free fetal DNA.

Thus, the present invention provides a method for determining the content of cell-free fetal DNA in a maternal peripheral blood sample, comprising:

(1) performing high-throughput single-end sequencing on plasma DNA extracted from the maternal peripheral blood to obtain resulting sequences;

(2) aligning said resulting sequences with a human reference genome to determine the numbering and localization of each resulting sequence in a chromosome, and (3) determining size distribution of plasma DNA based on the localization of each resulting sequence in a chromosome, and determining the content of cell-free fetal DNA based on its relationship with the size distribution of plasma DNA.

In one embodiment of the present invention, said step (1) comprises: extracting plasma DNA from the maternal peripheral blood, constructing a library and performing high-throughput single-end sequencing using said library to obtain resulting sequences.

In one embodiment of the present invention, reads of the high-throughput single-end sequencing is shorter than the size of cell-free fetal DNA, preferably shorter than 166 p, more preferably is from 30 bp to 50 bp.

In one embodiment of the present invention, the construction of a library is free of PCR amplification, which enables the library finally used in sequencing to keep the sample DNA in original condition without introducing any DNA sequence modification caused by PCR (such as mutation) and will not dilute valid data. Thus, constructing a library without PCR amplification ensures the accuracy of the sequencing data, shortens the time needed for constructing a library and saves cost.

In one embodiment of the present invention, each sample has at least 4M resulting sequences.

In one embodiment of the present invention, the ratio between the number of nucleotide sequences anchored on a chip and the number of loaded DNA molecules during sequencing is at least 0.1%. This ratio also represents the ratio between the number of molecules that can be detected and the total number of loaded molecules. If this ratio is less than 0.1%, the probability of detecting both ends of a DNA would not be high, thereby sufficient paired-end data cannot be obtained from the single-end sequencing results to calculate the size of detected DNA fragments.

In one embodiment of the present invention, the relationship between the content of cell-free fetal DNA and the size distribution of plasma DNA fragments is obtained by linear fitting the size distribution of plasma DNA fragments and the cell-free DNA content in a male fetus. As mentioned previously, in a male fetus, the content of cell-free fetal DNA can be easily calculated based on the percentage of chromosome Y sequence reads relative to the reads aligned to autosomes (chrY %).

In one embodiment of the present invention, the size distribution of plasma DNA fragments refers to the ratio between the fragments with a size of 100-150 bp and the fragments with a size of 163-169 bp.

In another aspect, the present invention provides a device for determining the content of cell-free fetal DNA in a maternal peripheral blood sample, comprising:

a detection module, for performing high-throughput single-end sequencing on plasma DNA extracted from the maternal peripheral blood to obtain resulting sequences, an alignment module, for aligning said resulting sequences with a human reference genome to determine the numbering and localization of each resulting sequence in a chromosome, a calculation module, for determining size distribution of plasma DNA based on the localization of each resulting sequence in a chromosome, and determining the content of cell-free fetal DNA based on its relationship with the size distribution of plasma DNA; and an output module, for outputting the content of fetal cell-free DNA.

In one embodiment of the present invention, the detection module of the present invention is any platform that can be used for high-throughput single-end sequencing known in the art, for example, cBot instrument from Illumina, Genome Analyzer or NextSeq CN500 sequencer from Illumina, or sequencer of SOLiD series from ABI. The alignment module of the present invention includes various alignment softwares known by one skilled in the art, such as Bowtie, Bowtie2, BWA, Subread and the like.

One skilled in the art understand that, some modules or some steps of the invention as described above can be achieved by common computing devices. They can be assembled on a single computing device, or be arranged on an internet comprising multiple computing devices. Optionally, they can be realized by executing program codes in computing devices. Thus, they can be stored in a storing device and executed by a computing device, or can be made in several integrated circuit modules respectively. Alternatively, multiple modules or steps can be realized by making them into a single integrated circuit module. Therefore, the present invention is not limited to any combination of specific hardware and software.

Thus, while obtaining the results of a noninvasive prenatal testing by high-throughput single-end sequencing, the present invention evaluates the reliability of said prenatal testing by determining the content of cell-free fetal DNA. In other words, in addition to the high-throughput sequencing, the method of the invention does not require any other experimental operation to provide an important index for assessing the reliability of the prenatal testing.

FIGURES

FIG. 1 is a diagram showing the size distribution of cell-free fetal DNA fragments in a sample. PE: size distribution based on a pair-end sequencing results. SE: size distribution calculated from a single-end sequencing results.

EXAMPLES

Figure 1:
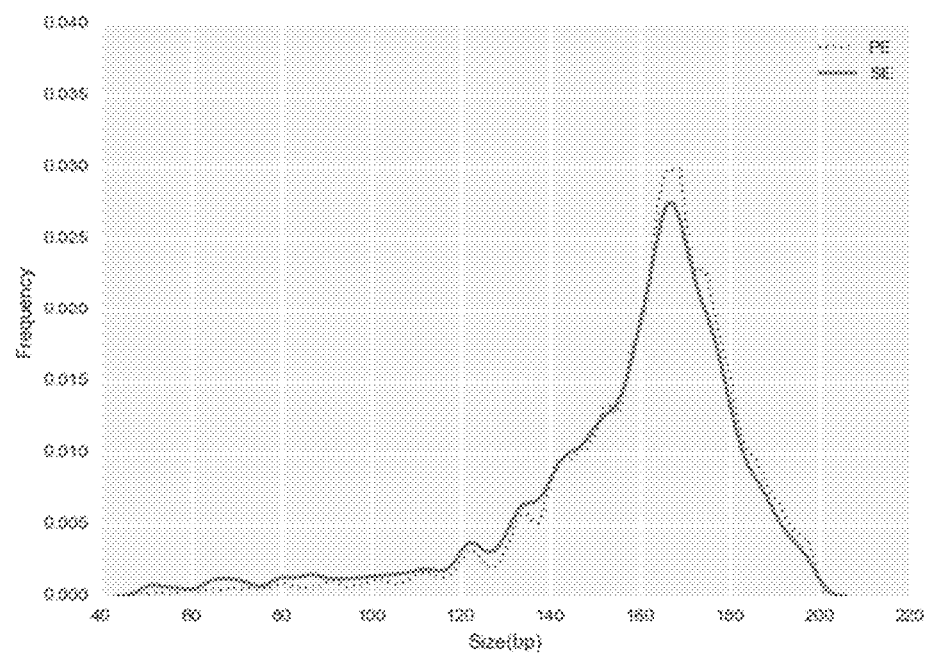

The present invention will be further illustrated by referring to the figures and the following examples. One skilled in the art will understand that the figures and examples are merely for the purpose of illustration, and will not limit the scope of the present invention in any way. Examples and features within the examples can be combined with each other without contradiction.

Example 1

Comparison Between the Results of Paired-End Sequencing and the Results Calculated from Single-End Data In this example, a maternal plasma DNA sample was subjected to paired-end sequencing, and the results thereof are used to count the size distribution of cell-free fetal DNA fragments and then plotted. At the same time, single-end data was obtained from the paired-end sequencing results, and the size distribution of cell-free fetal DNA fragments was calculated from the obtained single-end data and then plotted. The following shows a specific example wherein the maternal plasma DNA was sequenced and analyzed.

Step 1: DNA extraction. About 5 ng plasma DNA was extracted from the maternal peripheral blood.

Step 2: End filling and adding poly-adenine (poly-A) tail. The reaction mixture was prepared as follows:

TABLE 1

| | |
|---|---|
| Plasma DNA solution | 41.5 μl |
| T4 DNA polymerase buffer (10×) | 5 μl |
| 10 mM dNTP mixture | 2 μl |
| T4 DNA polymerase | 1 μl |
| Taq polymerase | 0.5 μl |
| Total volume | 50 μl |

The mixture was placed in a 37° C. warm bath for 20 min (for end-filling), and then transferred to a 72° C. warm bath for 20 min (for addition of poly-A tail). Purification was not needed at this time.

Step 3: Linker ligation. The reaction mixture was prepared as follows by adding additional reaction agents into the solution obtained in step 2:

TABLE 2

| | |
|---|---|
| Plasma DNA (from step 2) | 50 μl |
| Reaction buffer for quick ligation (10×) | 10 μl |

TABLE 2-continued

| | |
|---|---|
| DNA linker | 2 μl |
| Quick T4 DNA ligase (NEB) | 1 μl |
| Sterile H$_2$O | 37 μl |
| Total volume | 100 μl |

The mixture was placed in a 20° C. warm bath for 15 min, and then transferred to a 65° C. warm bath for additional 10 min, and finally was kept at 4° C. The ligated plasma DNA was recovered using Beckman Ampure XP beads and eluted with 22 μl sterile dH$_2$O or an elution buffer, so as to obtain a library. The DNA linkers used in this step includes a first-end linker and a second-end linker, which have different labels.

Step 4: Quantification of the library and mixing. 1 μl prepared library was taken for qPCR quantification, and a concentration higher than or equal to 20 pM means the quality of the library is good. According to arrangement of channels, 96 libraries with different linkers in the same channel were mixed with equal amount. 1 μl mixed samples was used for qPCR quantification.

Step 5: Sequencing. The mixed library was diluted to 2.5 pmol/L based on the above qPCR quantification results. 1.3 mL sample was loaded according to the instructions of NextSeq CN50 to perform a 36 bp paired-end sequencing.

Step 6: Analysis of the sequencing results. The paired-end sequencing results were aligned to the reference human genome. The size of a DNA fragment was calculated as the subtraction result of the aligned positions of two ends of the same DNA fragment. The size distribution of DNA fragments was counted and plotted (see FIG. 1, PE). Sequences aligned to sex chromosomes and mitochondrion were excluded here.

Step 7: Calculation of size distribution of DNA fragments using single-end data. Sequencing data from the first-end linker (similar results were obtained with sequencing data from the second-end linker) was extracted from the paired-end sequencing results based on different labels, which was further aligned to the human reference genome sequence, and the numbering as well as localization of each detected sequence in chromosomes were recorded. Two sequences which were aligned to the same chromosome with a relatively short distance (considering that the cell-free fetal DNA generally is shorter than 200 bp and most has a size around 167 bp, the selected distance herein was 200 bp or less) were selected to calculate the size of DNA fragments. Sequences aligned to sex chromosomes and mitochondrion were excluded here. If the alignment orientation of the 36 bp sequence is forward, then it is recorded as F, otherwise it is recorded as R. Two sequences aligned to a relatively short distance may come from the same DNA fragment (i.e. "paired-end" signal) or may be just two unrelated DNA fragments happened to have a close distribution distance (i.e. base event). If the signal comes from both ends of the same DNA fragment, the alignment orientations thereof should be opposite and direct inwards (recorded as FR). In other words, regarding the same reference sequence, the 36 bp sequence aligned to the front part is forward, and that aligned to the later part is reverse. However, the base event in which DNA fragments were randomly distributed has no bias in alignment orientation. Thus, it is reasonable to assume that the base event has an even distribution among the 4 combinations of various alignment orientations of two sequences (i.e. FR, RF, FF, and RR). Based on the above analysis, all events can be classified as four groups according to the alignment orientation of two 36 bp sequences, wherein FR includes paired-end signals and base events, while RF, FF and RR only include base events, and the number of base events in FR, RF, FF and RR should be the same. Therefore, the average number of RF, FF and RR can be counted to estimate the number of base events in FR, thereby obtaining the "paired-end" signal by subtracting the base events from the total FR events. Finally, the size distribution of fragments can be obtained by analysing said "paired-end" signal (see FIG. 1, SE).

As shown in FIG. 1, the size distribution of fragments directly obtained from the paired-end sequencing results of said sample generally is in line with that obtained from calculation based on single-end data in terms of overall trend, although the single-end data fluctuates largely relative to the paired-end sequencing results due to significantly smaller quantity of available data. The results show that, analysis based on single-end data of the invention can well represent the actual distribution of DNA fragments in maternal plasma.

Example 2

The Relationship of the Content of Cell-Free Fetal DNA with the Size Distribution of Plasma DNA Fragments Calculated Based on Single-End Sequencing Results Male fetus were selected as training set, and the content of cell-free fetal DNA cff % thereof were calculated by alignment to chromosome Y (chrY). As the accuracy of this chrY method is positively correlated to the size of sequencing data, samples with sufficient data should be selected to ensure the accuracy of the calculation results in the training set. This example selected totally 130 samples with a sequencing data size larger than 6M reads. The example was carried out as follows:

1: Library was prepared and subjected to high-throughput sequencing as described in steps 1-5 of Example 1, the only difference being that this example used 36 bp single-end sequencing instead of paired-end sequencing.

2: As described in steps 6-7 of Example 1, the size distribution of DNA fragments in maternal plasma was calculated.

3: Size ratio (SR) was calculated as follows based on the obtained results:

$$SR=P(100\text{-}150)/P(163\text{-}169),$$

Wherein P (100-150) refers to the percentage of fragments with a size of 100-150 bp, and P (163-169) refers to the percentage of fragments with a size of 163-169 bp.

4: The size distribution of fragments and the content of cell-free fetal DNA in each sample of the training set were linearly fitted using the least square method, namely SR=a+b*cff %, wherein "a" represents the intercept, and "b" represents the slope.

Figure 2:
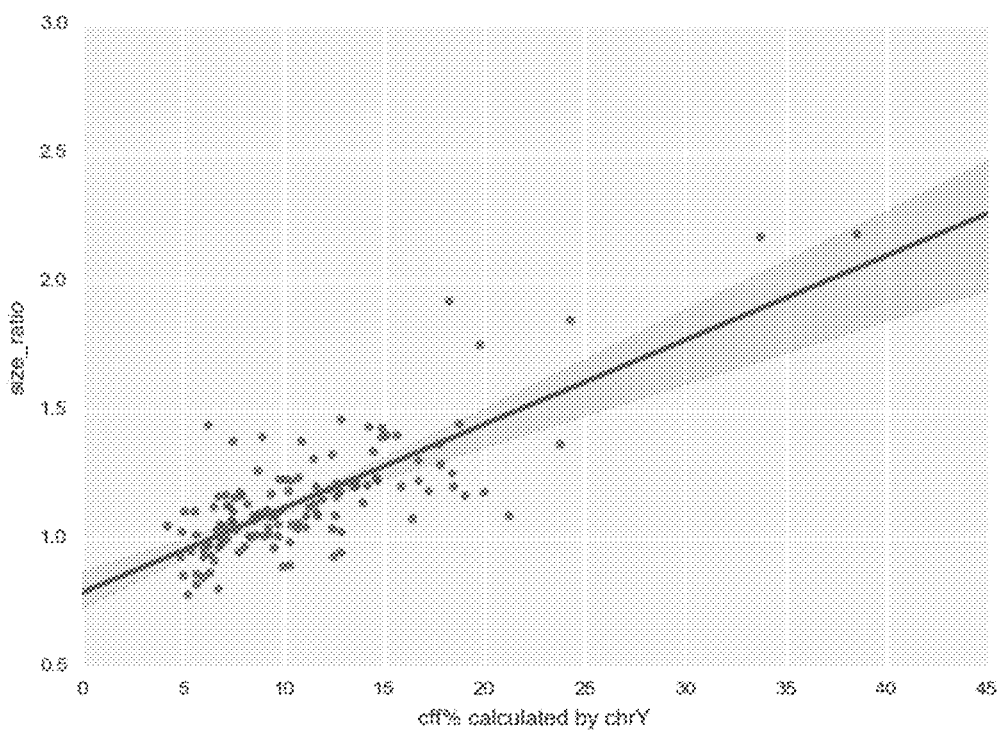
FIG. 2 is a diagram showing the relationship of size distribution calculated from the single-end sequencing results with the content of cell-free fetal DNA.

The linear fitting results are shown in FIG. 2. Regarding the fitting parameters, the intercept is 0.7890, the slope is 0.0328, and the correlation coefficient R is 0.768.

5: The fitting parameters obtained above can be used to calculate the content of cell-free fetal DNA according to the following formula:

$$cff\%=(SR-a)/b.$$

Example 3

Calculation of the Content of Cell-Free Fetal DNA in Female Fetuses

In this example, the content of cell-free fetal DNA in 40 samples from female fetuses was calculated using the fitting parameters obtained in Example 2.

1: Library was prepared and subjected to high-throughput sequencing as described in steps 1-5 of Example 1, the only difference being that this example used 36 bp single-end sequencing instead of paired-end sequencing.

2: As described in steps 6-7 of Example 1, the size distribution of DNA fragments in maternal plasma was calculated.

3: Size ratio (SR) was calculated as follows based on the obtained results:

$$SR=P(100\text{-}150)/P(163\text{-}169).$$

4: The content of cell-free fetal DNA was calculated using the fitting parameters "a" and "b" obtained in Example 2: cff %=(SR−a)/b.

The calculated results of each sample are shown in Table 1.

TABLE 1

| Sample | cff % | Sample | cff % |
|---|---|---|---|
| 15X68293 | 4.42 | 16C53371 | 2.27 |
| 16C19525 | 0.56 | 16C53372 | 10.97 |
| 16C24272 | 3.69 | 16C53373 | 12.34 |
| 16C25986 | 1.88 | 16C53939 | 6.57 |
| 16C25987 | 11.53 | 16C66221 | 5.23 |
| 16C38132 | 5.86 | 16TP7153 | 18.37 |
| 16C44182 | 2.89 | 16TP7157 | 23.63 |
| 16C44461 | 0.24 | 16X30049 | 12.74 |
| 16C44466 | 1.69 | 16X30151 | 9.59 |
| 16C44477 | 1.91 | 16X52580 | 9.18 |
| 16C49587 | 9.41 | 16X65375 | 2.30 |
| 16C52228 | 15.98 | 16X65387 | 9.56 |
| 16C52238 | 24.82 | 16X65388 | 10.55 |
| 16C52423 | 8.68 | 16X76901 | 11.76 |
| 16C52887 | 6.71 | 16X93849 | 5.44 |
| 16C52893 | 8.40 | 16X96193 | 10.12 |
| 16C53366 | 4.90 | 16X96741 | 11.47 |
| 16C53367 | 9.29 | Y15X69003 | 7.51 |
| 16C53369 | 13.37 | Y16C25860 | 17.43 |
| 16C53370 | 14.89 | Y16X94610 | 12.64 |

Example 4

Calculation of the Content of Cell-Free Fetal DNA in Male Fetuses

In this example, the content of cell-free fetal DNA in 20 samples from male fetuses was calculated using the fitting parameters obtained in Example 2.

1: Library was prepared and subjected to high-throughput sequencing as described in steps 1-5 of Example 1, the only difference being that this example used 36 bp single-end sequencing instead of paired-end sequencing.

2: As described in steps 6-7 of Example 1, the size distribution of DNA fragments in maternal plasma was calculated.

3: Size ratio (SR) was calculated as follows based on the obtained results:

$$SR=P(100\text{-}150)/P(163\text{-}169).$$

4: The content of cell-free fetal DNA was calculated using the fitting parameters "a" and "b" obtained in Example 2: cff %=(SR'−a)/b.

The following Table 2 shows the content of cell-free fetal DNA cff % in each sample calculated using the method of the invention and the method of alignment to chromosome Y (ChrY).

TABLE 2

| Sample | cff % calculated by ChrY | cff % calculated by the present invention |
|---|---|---|
| 15C44222 | 17.054 | 11.24 |
| 15C44663 | 12.439 | 16.224 |
| 15C54809 | 13.344 | 12.558 |
| 15C57852 | 6.508 | 7.836 |
| 15C61827 | 7.84 | 8.864 |
| 15C62515 | 10.883 | 8.979 |
| 15C63915 | 13.035 | 9.315 |
| 15C67942 | 13.474 | 10.01 |
| 15C68743 | 16.288 | 19.241 |
| 15C71040 | 5.843 | 4.87 |
| 15C79157 | 5.53 | 3.737 |
| 15C80858 | 21.437 | 20.744 |
| 15C81096 | 10.369 | 9.004 |
| 15C82765 | 10.407 | 7.114 |
| 15C82770 | 8.282 | 9.492 |
| 15C84218 | 16.022 | 13.88 |
| 15C84246 | 12.167 | 8.531 |
| 15C85236 | 8.94 | 13.705 |
| 15C85247 | 9.738 | 7.353 |
| 15C85412 | 6.843 | 6.213 |

Figure 3:
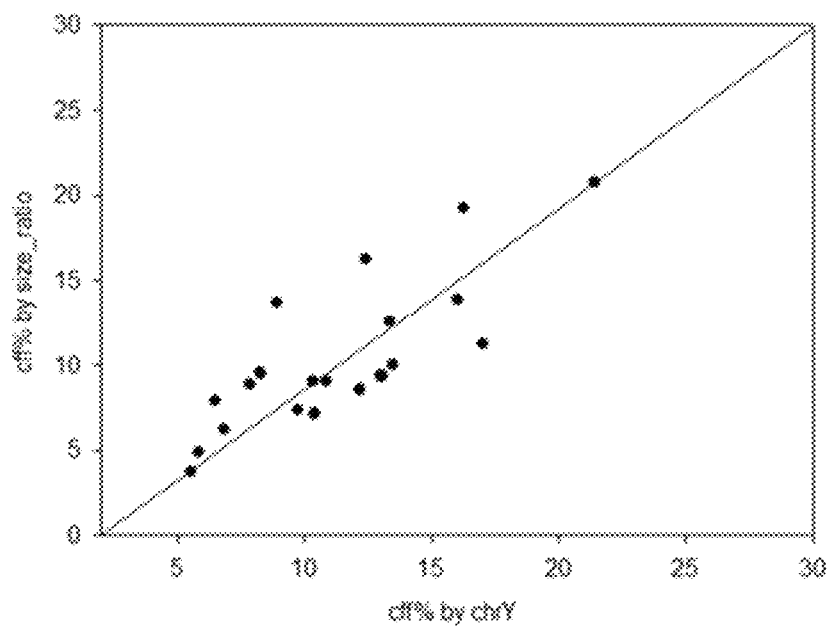
FIG. 3 is a diagram comparing the content of cell-free fetal DNA (cff %) calculated by the present invention and by the method of alignment to chromosome Y (ChrY).

All the data shown in Table 2 was plotted (see FIG. 3). As shown in FIG. 3, the content of cell-free fetal DNA calculated by the method of the present invention generally is in line with that calculated by the method of alignment to chromosome Y, indicating that the method of the present invention has a high accuracy.

It should be noted that the above examples are merely preferable embodiments of the invention, and do not intend to limit the invention in any way. One skilled in the art can understand that the present invention can have various modifications and changes. The reaction reagents, reacting conditions and the like involved in constructing a plasma DNA sequencing library can be adjusted and varied according to specific requirements accordingly. One skilled in the art can also understand that, within the spirit and principle of the invention, all modifications, equivalent replacements, improvements and the like are within the protection scope of the invention.

What is claimed is:

1. A method for determining the content of cell-free fetal DNA in a maternal peripheral blood sample, comprising:
    (1) performing high-throughput single-end sequencing on plasma DNA fragments extracted from the maternal peripheral blood sample to obtain resulting sequences,
        wherein the maternal peripheral blood sample has at least 4M resulting sequences;
    (2) aligning said resulting sequences with a human reference genome,
        wherein to determine the numbering and localization of each resulting sequence in a chromosome,
        two sequences with a distance of 200 bp or less, and the alignment orientations thereof being opposite but direct outwards are recorded as RF base events,
        the number of the RF base events are counted,
        two sequences with a distance of 200 bp or less, and the alignment orientations thereof being identical and direct forward are recorded as FF base events,
        the number of the FF base events are counted,
        two sequences with a distance of 200 bp or less, and the alignment orientations thereof being identical and direct reverse are recorded as RR base events,
        the number of the RR base events are counted,
        the average number of the number of the RF base events, the number of the FF base events, and the number of the RR base events are recorded as the number of base events,
        and the following events are recorded as FR base events: two sequences with a distance of 200 bp or less, and the alignment orientations thereof are opposite and direct inwards,
        the number of the FR base events are counted,
        and the number of paired-end signal events are obtained by subtracting the number of the base events from the number of the FR base events,
        distribution of the paired-end signal events are obtained based on distribution of the base events,
        and the paired-end signal events are regarded as coming from the same DNA fragments; and
    (3) determining size distribution of plasma DNA fragments based on the paired-end signal events,
        wherein the size distribution of plasma DNA fragments refers to the ratio between the fragments with a size of 100-150 bp and the fragments with a size of 163-169 bp,
        and determining the content of cell-free fetal DNA based on its relationship with the size distribution of plasma DNA fragments.

2. The method of claim 1, wherein the step (1) comprises: extracting plasma DNA fragments from the maternal peripheral blood, constructing a library and performing high-throughput single-end sequencing using said library to obtain resulting sequences.

3. The method of claim 1, characterized in that, reads of the high-throughput single-end sequencing is from 30 bp to 50 bp.

4. The method of claim 2, characterized in that the construction of said library is PCR-free.

5. The method of claim 1, characterized in that, the ratio between the number of nucleotide sequences anchored on a chip and the number of loaded DNA molecules during sequencing is at least 0.1%.

6. The method of claim 1, characterized in that, the relationship of the content of cell-free fetal DNA with the size distribution of plasma DNA fragments is obtained by linear fitting the size distribution of plasma DNA fragments and the content of cell-free fetal DNA in a male fetus.

* * * * *